US008641275B2

(12) United States Patent
Fenske et al.

(10) Patent No.: US 8,641,275 B2
(45) Date of Patent: Feb. 4, 2014

(54) UNIVERSAL DENTAL X-RAY SENSOR HOLDER

(75) Inventors: Lawrence Jon Fenske, Madison, WI (US); Gregory Falendysz, Sun Prairie, WI (US); John Aaron Miller, Sun Prairie, WI (US); Thomas Albert Sutrina, Rockford, IL (US); Cunjiang Cheng, Milwaukee, WI (US); Kimberly Clementz Brown, Huntley, IL (US)

(73) Assignee: DENTSPLY International Inc., York, PA (US)

( * ) Notice: Subject to any disclaimer, the term of this patent is extended or adjusted under 35 U.S.C. 154(b) by 469 days.

(21) Appl. No.: 12/787,898

(22) Filed: May 26, 2010

(65) Prior Publication Data

US 2011/0293073 A1 Dec. 1, 2011

(51) Int. Cl.
*A61B 6/14* (2006.01)
(52) U.S. Cl.
USPC ........................................................ 378/168
(58) Field of Classification Search
USPC .................................................. 378/168, 191
See application file for complete search history.

(56) References Cited

U.S. PATENT DOCUMENTS

| 1,576,477 | A | 3/1926 | Weins |
| 3,473,026 | A | 10/1969 | Updegrave |
| 4,075,494 | A | 2/1978 | Jesmyn |
| 4,569,071 | A | 2/1986 | Levin |
| 5,677,537 | A | 10/1997 | Pfeiffer |
| 6,041,102 | A | 3/2000 | Francsis |
| 6,652,141 | B1 | 11/2003 | Cianciosi |
| 8,142,074 | B2 * | 3/2012 | Schmulenson et al. ....... 378/170 |
| 2001/0055368 | A1 * | 12/2001 | Carroll .......................... 378/189 |
| 2002/0108219 | A1 * | 8/2002 | McAllister ...................... 24/536 |
| 2002/0183785 | A1 | 12/2002 | Howell et al. |
| 2004/0096040 | A1 | 5/2004 | Kilcher et al. |
| 2005/0013412 | A1 * | 1/2005 | Calderwood et al. ......... 378/170 |

FOREIGN PATENT DOCUMENTS

WO 2006089003 A2 8/2006

OTHER PUBLICATIONS

Xp-002381053—Eezee-Grip Digital Sensor Holder by Dentsply Rinn Dental Economics (on-line) Nov. 2005 Joseph A. Blaes.

* cited by examiner

*Primary Examiner* — Irakli Kiknadze
(74) *Attorney, Agent, or Firm* — David A. Zdurne; Douglas J. Hura; Leana Levin (57) ABSTRACT

A dental x-ray sensor holder includes at least two clamping faces wherein at least one of the faces includes at least one and preferably a plurality of resiliently deformable gripping protrusions. The clamping faces are positioned in a moveable, spaced opposing relation, such that the faces may be physically moved together to physically impinge the x-ray sensor therebetween.

16 Claims, 8 Drawing Sheets

UNIVERSAL DENTAL X-RAY SENSOR HOLDER

RELATED APPLICATIONS

This application claims the benefit of U.S. Ordinary application Ser. No. 11/998,745 filed on Nov. 30, 2007 which is a continuation application of Ser. No. 11/354,626 filed on Feb. 15, 2006 and U.S. Provisional Application Ser. No. 60/653,559 filed on Feb. 16, 2005 (RIN-013).

TECHNICAL FIELD

A dental x-ray sensor holder is provided. The holder is universal in that it is able to secure a wide variety of shapes and sizes of commercially available dental x-ray sensors. A plurality of resiliently deformable gripping protrusions are employed to secure such a variety of sensors.

BACKGROUND OF THE INVENTION

Dental professionals have employed x-ray imaging for many years. A traditional dental x-ray procedure includes exposing an x-ray film to x-ray energy after it has passed through the target site. The film is developed and an image of the target site is achieved. It has also long been known that in order to obtain a useful image, the dental x-ray film must be positioned relative to the target site in a predetermined and secure manner. Many numbers of x-ray film holders and positioning devices have been developed, including for example, that shown in U.S. Pat. No. 3,473,026 which is hereby incorporated by reference for background purposes.

In more recent history, many dental professionals have used digital x-ray sensors in place of traditional x-ray films. An example of such a sensor is shown for example in U.S. Pat. No. 6,652,141 which is hereby incorporated by reference for background disclosure of x-ray sensors. As with x-ray films, it is necessary for the x-ray sensor to be secured in a predetermined position during the x-ray imaging procedure. In a manner similar to the use of x-ray films, holding and positioning devices have been developed for x-ray sensors.

Unlike x-ray films however, it has occurred that different x-ray sensors required for different uses also have different shapes and sizes. X-ray films tended to be of substantially similar size and shape whether the professional was attempting to image a posterior tooth, and anterior tooth or some other location in the oral cavity. With x-ray sensors however, it appears that the general size and shape of the sensors used for these different procedures are also different. In fact, even common target sites can be imaged with x-ray sensors having a different size and shape as may be offered by different manufacturers. The reason for this, while not a limitation of the present invention, seems to be caused at least in part by the fact that different sensors often use different sensing components even if used for imaging the same target site. Hence, because of the different internal components the size and shape of the resulting sensor, and perhaps more importantly for purposes of the present invention, its outside housing will greatly vary.

Because of this difference between sensors it is a standard practice to provide holder that is configured for use with only one type of sensor, or more to the point, one size and shape of sensor. This may work for the intended purpose but requires the dental professional to purchase, store and choose from between a large number of sensor holders. This is an expensive and time consuming requirement at best.

A need exists therefore, for a sensor holder than can be employed with a wide variety of x-ray sensor sizes and shapes. Such would require the dental professional to employ only one sensor holder where in the past would have required a plurality of such holders.

SUMMARY OF THE INVENTION

It is therefore, an object of the present invention to provide a dental sensor holder, particularly one useful with a wide variety of sizes and shapes of digital dental x-ray sensors.

These and other objects of the invention which shall become apparent from the description and drawings herein, are achieved by the invention as herein described, shown and claimed.

In general a dental x-ray sensor holder comprises a at least two clamping faces wherein at least one of the faces includes at least one and preferably a plurality of resiliently deformable gripping protrusions. The clamping faces are positioned in a moveable, spaced opposing relation, such that the faces may be physically moved together to physically impinge the x-ray sensor therebetween.

PREFERRED EMBODIMENTS FOR CARRYING OUT THE INVENTION

Figure 5:
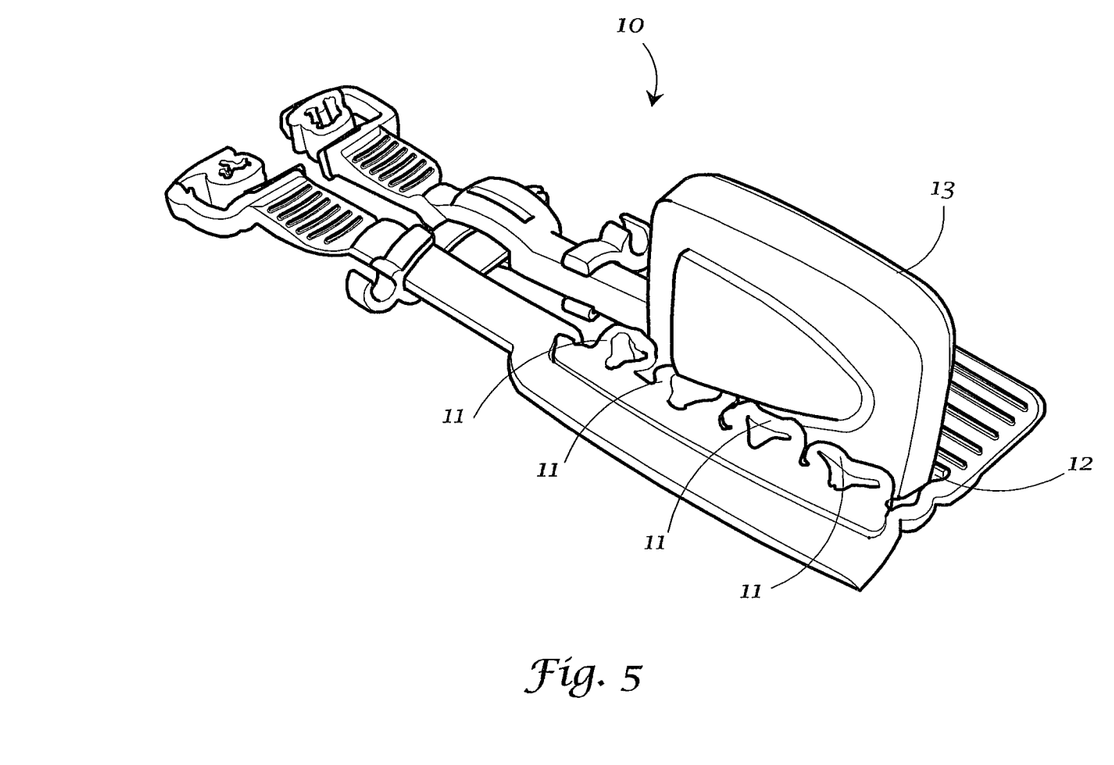
FIG. 5 is a perspective view of a sensor holder as in FIG. 1, showing the holder in a closed position with a sensor held therein, the sensor being shown for environmental purposes.

A sensor holder embodying the concepts of the present invention is generally shown by way of example on the drawings by the number 10. Sensor holder 10 is provided with at least one resiliently deformable gripping protrusion 11. Some mechanism, as will be more fully developed below, is provided such that the at least protrusion 11 and more preferably a plurality of protrusions 11, are moveable toward a blocking surface 12 such that a sensor such as sensor 13 (FIG. 5) is physically contacted by protrusions 11 and blocking surface 12. Protrusions 11 are sufficiently deformable that the physical contact causes protrusions 11 to at least partially deform thereby at least partially conforming to the outer shape of the position of sensor 13 with which protrusions 11 are in contact. Further, protrusions 11 are also of sufficient resiliency such that such deformation is at least partially resisted by protrusions 11, thereby exerting a resilient force upon sensor 13. By "sufficient resiliency" it is meant enough to hold sensor 13 in a predetermined position and with enough force to hold sensor 13 for a given procedure, such as a dental x-ray.

Protrusions 11 may be of any shape or size and may be formed from any suitable material such as a rubber, plastic or other material. As depicted by way of example on the drawings, protrusions 11 are generally round but may be square, triangular, rectangular, cone-shaped, truncated cone shaped, spherical, box-like, irregularly shaped or the like. It will also be appreciated that when plurality of protrusions 11 are employed, they may be regularly or irregularly spaced upon holder 10, although only a regularly shaped plurality of protrusions 11 are shown on the drawings for simplicity sake.

Figure 4:
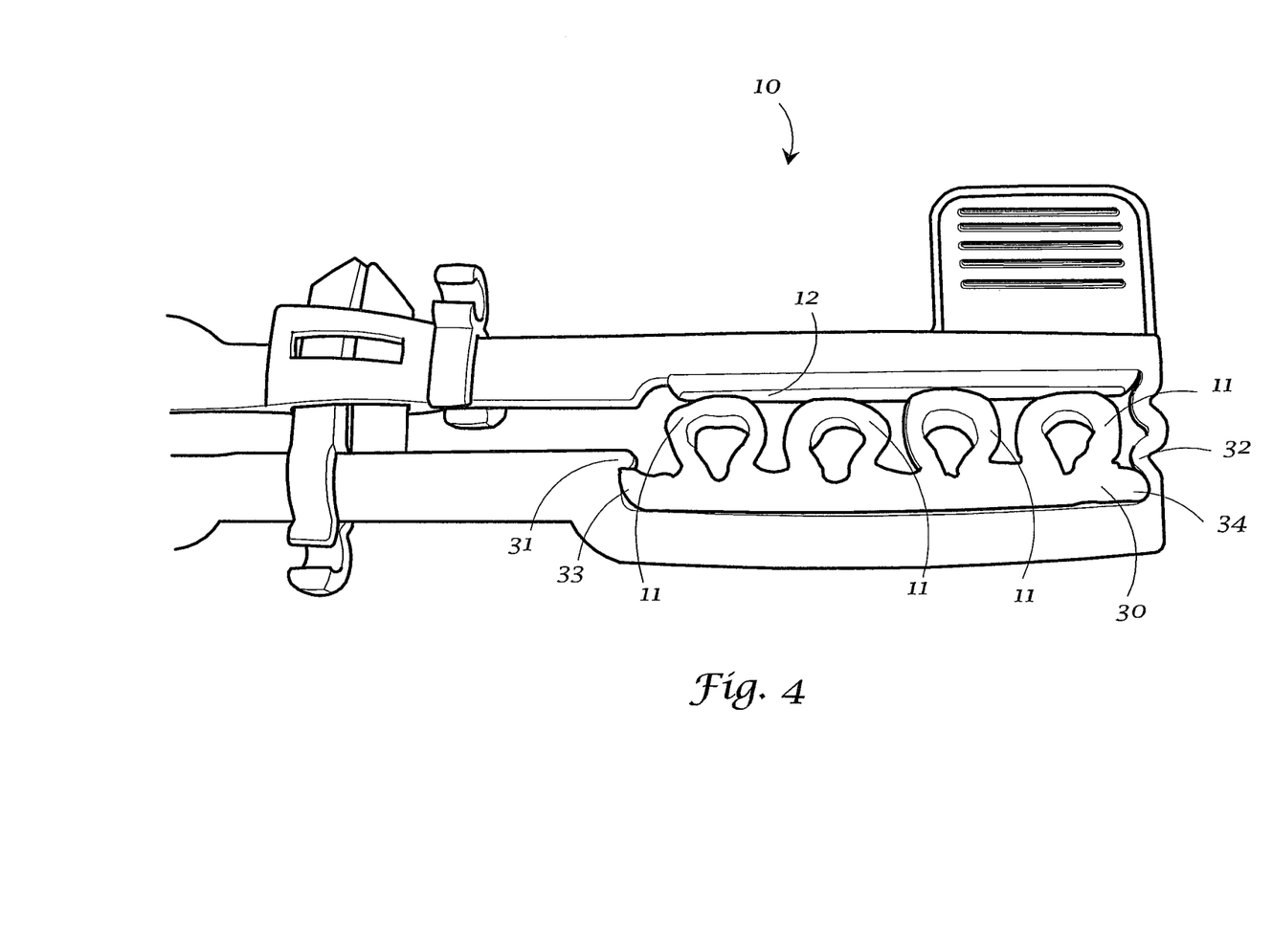
FIG. 4 is a close-up, perspective view of one portion of the sensor holder of FIG. 3, showing the cord clip attached to the holder and showing the holder in a closed position without a sensor.

One preferred protrusion is a ring 20 having a hollow interior portion 21. As shown for example in FIGS. 4 and 5, hollow interior 21 facilitates deformation of protrusions 11 because there is less material in hollow area 21 than there would be if protrusion 11 were otherwise solid. Of course, solid protrusions 12 (not shown) are within the scope of the invention as long as they are otherwise sufficiently deformable and resilient.

The material chosen to fabricate a given protrusion 11, as well as the size, shape and other structure of protrusion 11 are preferably chosen such that sensors of varying size and shape can be held within holder 10. As is known in the industry, sensors 13 often vary in thickness, shape and size, and may also vary with respect to for example, the means of attaching a connecting cord or wire. It has been unexpectedly found that by using at least one protrusion 11, a wide variety of such sensors can be held by holder 10 in a manner suitable for the intended use of the sensor. Hence, it will be appreciated that a holder 10 having such a protrusion 11 is "universal" in that it can accommodate more than one such sensor.

As stated above, it is preferred that a protrusion 11 be moveable toward a blocking surface 12. Of course, blocking surface 12 may be moveable toward a protrusion 11 or a protrusion 11 and a blocking surface 12 may be moveable toward each other, all of which are within the scope of the present invention. In use, blocking surface 12 cooperates with at least one protrusion 11 so as to physically contact and impinge upon a sensor 13 so as to trap or otherwise hold sensor 13 therebetween, when the protrusion 11 and the blocking surface 12 are brought toward each other, which is the closed position of the holder 10. Of course, blocking surface 12 may itself be a protrusion 11 (not shown) but is preferably a flat surface made of any suitable material. Blocking surface 12 for example, can be integrally fabricated with and from the same material as holder 10 or it may be fabricated from a different material such as a rubber, plastic or other suitable material and may even be fabricated from the same material as protrusion 11.

Although protrusions 11 may be integrally formed with holder 10, in a preferred embodiment of the invention, a plurality of protrusions 11 of suitable shape and size are fabricated from a soft rubber or other elastomeric material, as is blocking surface 12. The plurality of protrusions 11 are further fabricated as one piece, wherein each protrusion 11 is spaced upon a base member 30. Although it is only one preferred example, the drawings depict a plurality of protrusions 11 of a ring design and regularly spaced in a substantially planar fashion upon a base member 30. Base member 30 and hence protrusions 11 are affixed to holder 10 in any suitable manner. For example, base member 30 may be adhesively fixed, welded or otherwise bonded to holder 10 in a location such that protrusions 11 are caused to be in a spaced opposing relation to blocking surface 12. In another embodiment, holder 10 is provided with a locating tab 31 and even a second locating tab 32. Cooperating tabs 33 and 34 on base member 30 physically engage tabs 31 and 32 to thereby position or even restrain base 30 on holder 10 in a predetermined position.

Figure 1:
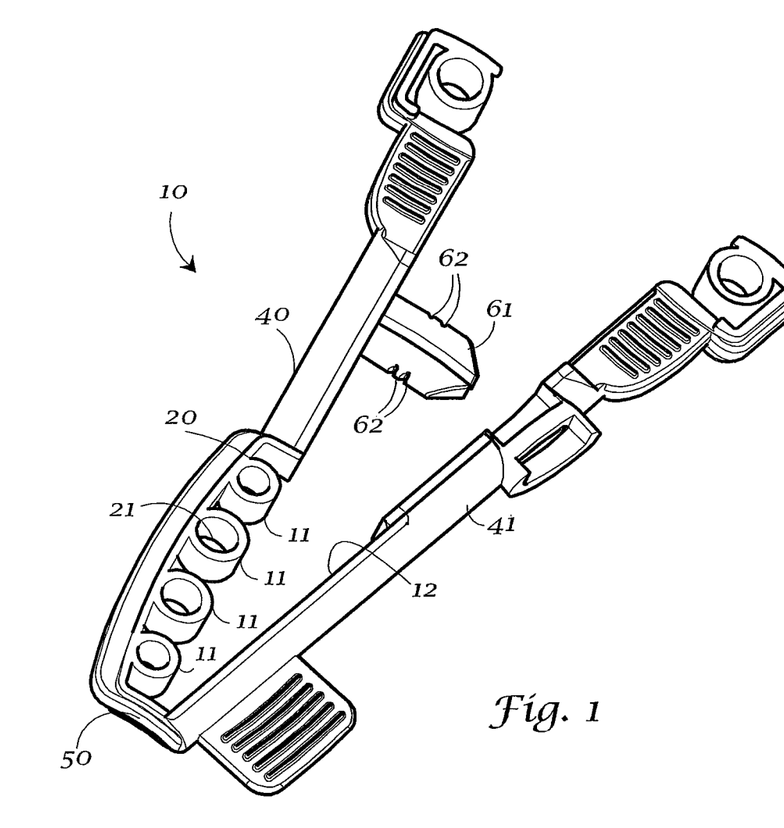
FIG. 1 is a perspective view of one side of a sensor holder according to the present invention, and showing the holder in an open position.
Figure 2:
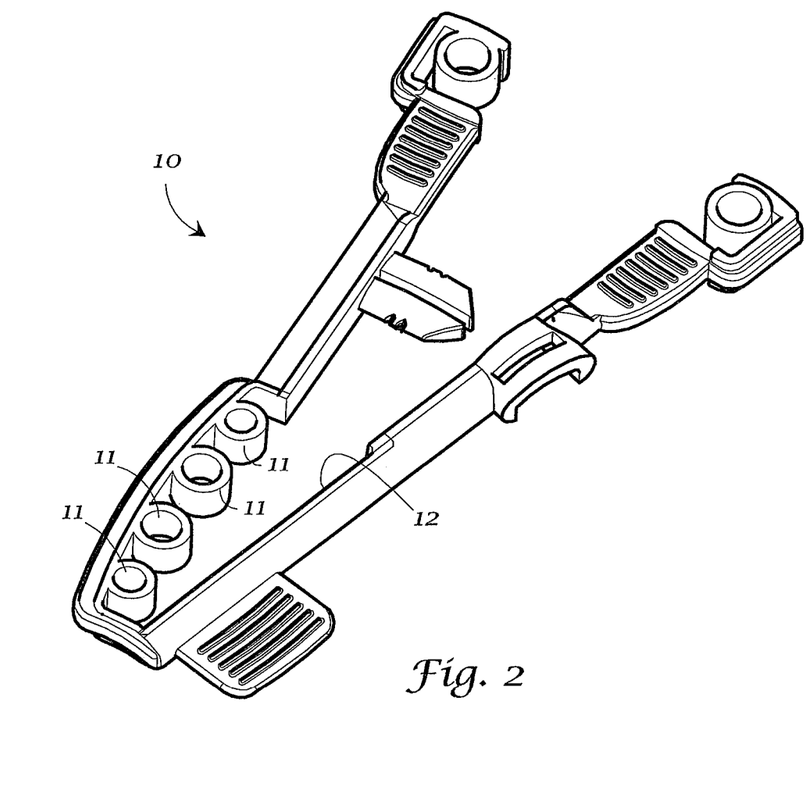
FIG. 2 is a perspective view of the opposite side of the sensor holder of FIG. 1.
Figure 3:
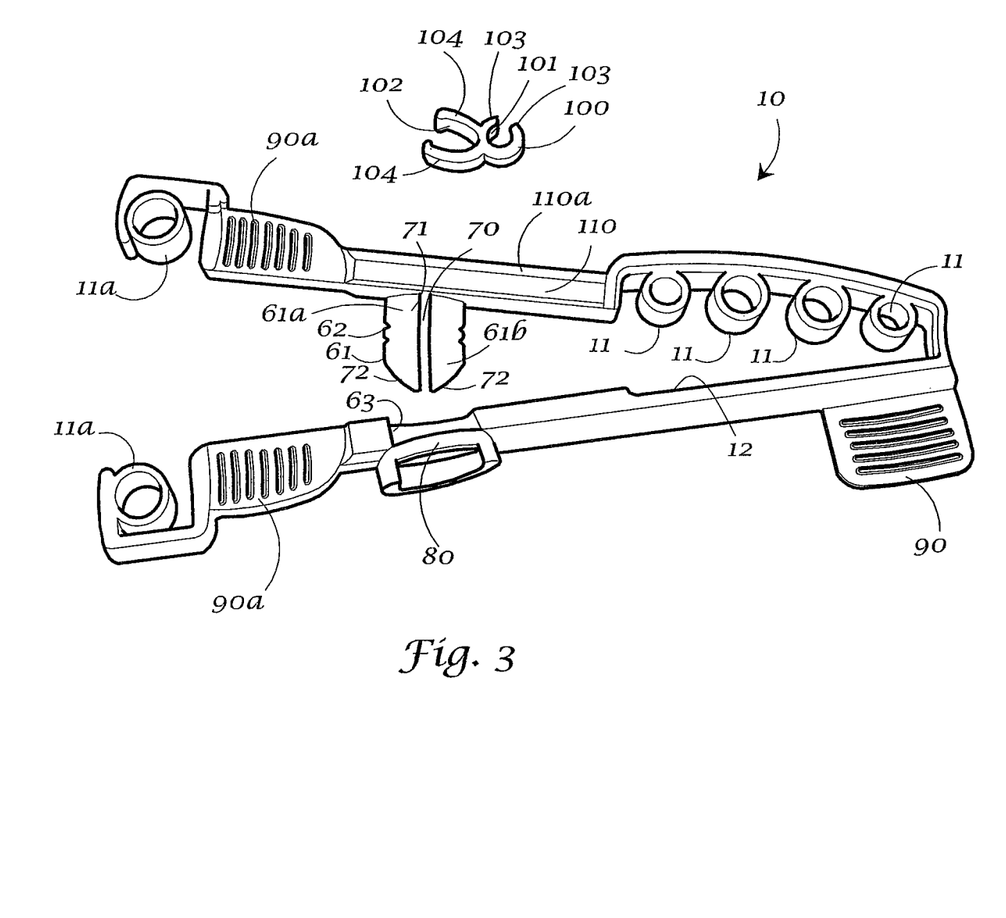
FIG. 3 is a perspective view of the sensor holder of FIG. 1 shown together with a detached cord clip.

Any means of moving either a protrusion 11, blocking surface 12 or both is within the scope of the invention. In a preferred embodiment, this includes a first leg 40 and a second leg 41 hingedly connected to each other. First leg 40 may carry for example, protrusion 11 while second leg 41 may carry blocking surface 12. By being hingedly connected in an appropriate location, such as at one end of holder 10, legs 40 and 41 and hence protrusion 11 and blocking surface 12 can be moved toward each other, that is toward the closed position, or away from each other, that is to the open position, as shown for example, FIGS. 6 and 1 respectively. By physically contacting sensor 13 between a protrusion 11 and blocking surface 12, the sensor is securely held or clamped therebetween.

In one embodiment of a hinge, hinge 50 is a living hinge integrally formed with holder 10. Of course, any hinge including for example a traditional pin and collar (not shown) is within the scope of the present invention. Living hinge 50 is preferred for simplicity. It will be appreciated that holder 10 may have a hinge placed such that holder 10 scissors-shaped and operates in a scissors manner, although such a configuration is not shown on the drawings.

It is preferred to provide some means of securing holder 10 in its closed position, especially because it is standard procedure for dental professionals to remove themselves from the immediate area of the patient during a given x-ray procedure. Any means of so securing holder 10 is within the scope of the invention, including for example, adhesives, rubber bands, clamps, pins, other holders or fasteners or the like. It is preferred for simplicity to integrally form a securing mechanism 60 holder 10. One preferred securing mechanism 60 includes a ratchet member 61 having spaced detents 62, engageable with and operatively cooperable with at least one lug 63. As leg 40 is moved toward leg 41, or as the two are moved toward each other about hinge 50, ratchet member 61 is caused to physically engage and slide past lug 63 until a detent 61 is aligned therewith where lug 63 is then caused to engage detent 62 to secure holder 10 in the closed position.

More preferably, ratchet member 62 is provided with a first ratchet member arm 61a and a second ratchet member arm 61b, preferably of mirror image and spaced in an opposing relation with a void 70 therebetween and upon leg 40 or leg 41. At least one of and preferably both ratchet member arms 61a and 61b are provided with a connecting side 71 proximate to and preferably integrally formed with leg 40 or 41 upon which they are attached. Further, at least one and preferably both ratchet arms 61a and 61b are provided with a camming surface 72 at an end distal to connecting sides 71. The leg 40 or 41 to which the ratchet member 61 is not attached (that is, leg 41 in the drawings) is preferably provided with a constrictor such as constrictor ring 80, sized and shaped such that as ratchet member 61 is moved toward constrictor ring 80, camming surfaces 72 physically engage constrictor ring 80. Ratchet arms 61a and 61b would thereby be caused to move toward each other. By sizing and shaping ratchet arms 61a and 61b, and by choosing a suitable material for their construction, ratchet arms 61a and 61b are preferably resiliently deformable such that they move toward each other as camming surfaces 72 engage constrictor ring 80. As detents 62 align with lugs 63, the resilient nature of ratchet arms 61a and 61b will cause detents 62 and lugs 63 to physically engage thereby securing holder 10 in the closed position. To release holder 10 such that it can then be moved to its open position, a user would manipulate camming surfaces 72 to move ratchet arms 61a and 61b away from each other a suitable amount to allow lugs 63 and detents 62 to disengage. Lugs 63 and or detents 62 may be deformable to more easily permit engaging and disengaging. Of course, either ratchet member 61 or the leg opposite may alternatively carry lugs 2 and/or detents 63.

It will be appreciated that by provided a plurality of detents such as detents 62, a user may close holder 10 and secure holder 10 in its closed position to a degree that the user judges is sufficient so that sufficient force is placed upon sensor 13 held therein. For one sensor this might require one detent, and for another it may require a different detent to thereby selectively secure holder 10 in the required position, all of which are considered to be closed positions. Of course, if ratchet arm 61 only carried a mechanism to secure legs 40 and 41 in one position with respect to each other, this would still be within the scope of the invention. In such a case, ratchet arm 61 would not be a true ratchet, but would still function to secure holder 10 in its closed position. This is not depicted in the drawings.

Figure 6:
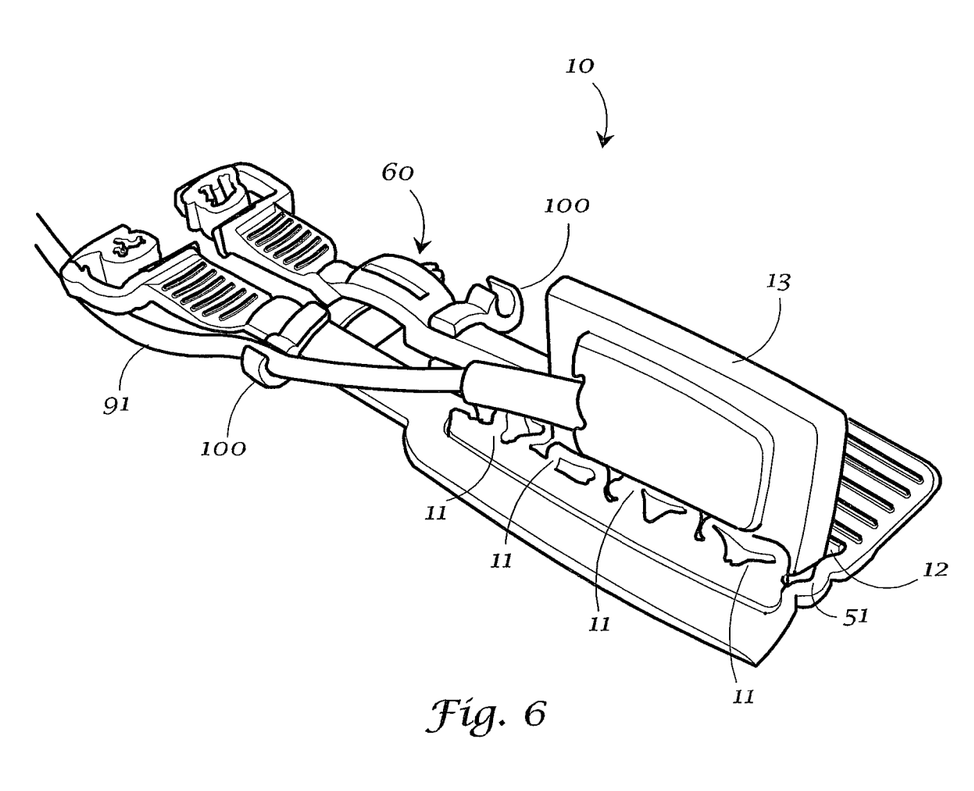
FIG. 6 is a perspective view as in FIG. 5, showing an alternative sensor having an attached cable, the sensor and its cable being shown for environmental purposes.
Figure 7:
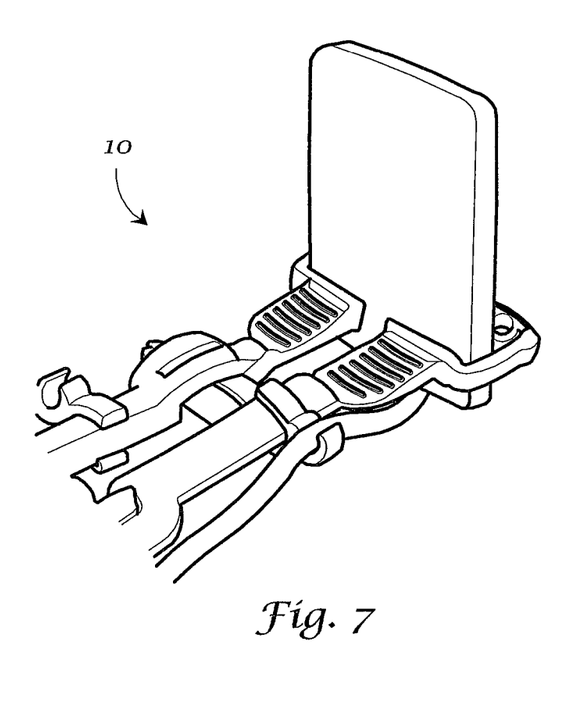
FIG. 7 is a close-up, perspective view of one portion of the sensor holder of FIG. 3, showing the cord clip attached to the holder and showing the holder in a closed position at the end opposite that of FIG. 4, and showing a sensor having a cable being held therein, the sensor and its cable being shown for environmental purposes.

Dental x-ray positioners are routinely provided with bit blocks such that a patient bites the bite block with their teeth to secure the holder and hence the x-ray film or sensor. Similarly, holder 10 according to the present invention is provided with a bite block 90. Further, sensors such as sensors 13 are often provided with a connecting cable such as cable 91 (FIG. 6). It is desirable to provide a structure to secure and position cable 90 during a given x-ray procedure. A clip such as clip 100 is provided according to the present invention. Clips are known in the industry and are often integrally formed with a holder or its associated structure. However, it is an aspect of the present invention to provide a clip that can secure a sensor cable 91 in a plurality of positions. By being so adjustable, the holder 10 is again capable of being used with more than one design of sensor 13, and hence again is universal. One or more clips 100 are preferably, removably fixable to holder 10 in a variety of positions. An integrally formed, non-adjustable clip 100a is shown for example on FIG. 4.

An adjustable clip 100 according to the invention, is preferably provided with a first clip surface 101 and a second clip surface 102. Clip surfaces 101 and 102 are preferably formed from arms 103 and 104 respectively. It is further preferred that a longitudinal clip attachment area 110 is provided upon at least one and perhaps even both legs 40 and 41. Clip attachment area 110 is configured to matingly engage clip arms 104 such that the cooperative and physical interaction therebetween causes clip 100 to be secured to clip attachment area 110. By having a longitudinal expanse, it will be understood that clip 100 may be placed at any number of locations upon clip area 110. Wire 91 can be clipped in a similar manner within arms 103. Arms 104 may even be provided with lips 105 to more securely physically engage an upstanding wall 110a of clip area 110.

For economy of purpose, it is desirable that holder 10 be provided with more than one protrusion 11, and in fact, may be provided with more than one area of holder 10 useful for holding a sensor 13. For example, at an end of holder 10 opposite that generally proximate to protrusion 11, a second protrusion 11a may be provided. In the configuration of holder 10 depicted in the drawings, protrusions 11 and bite block 90 are generally configured to be useful with a bitewing x-ray procedure. Protrusions 11a at the opposite side of holder 10 are generally configured to be used with a periapical imaging procedures. Proximate to protrusions 11a are suitable bite blocks 90a. By way of example, the periapical procedure area employing protrusions 11a does not employ a blocking surface such as blocking surface 12, but rather the two protrusions 11a serve the same purpose. It is understood of course that one leg 40 or 41 may carry a protrusion 11a while the opposed surface of the opposite leg may carry a blocking surface similar in design and function to blocking surface 12, if desired.

Figure 8:
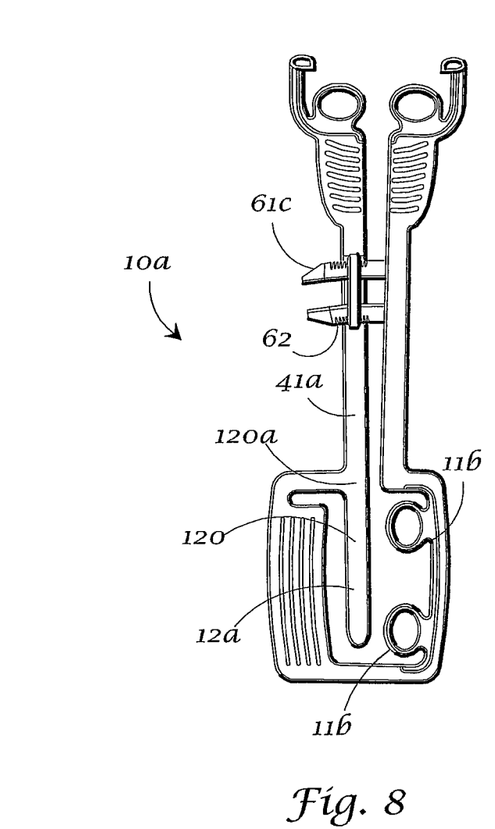
FIG. 8 is a top plan view of an alternative embodiment of a sensor holder according to the invention.

FIG. 8 shows an alternative embodiment of a sensor holder 10a according to the invention. Sensor holder 10a has a ratchet member 61c having a plurality of ratchet detents 62a. Further, holder 10a is provided with a bitewing area plurality of protrusions 11b, namely, two generally oval shaped protrusions 11b.

Holder 10a is also provided with a blocking surface 12a that is not affixed to its supporting leg along its entire length, as is the case with holder 10. Rather, blocking surface 12a of holder 10a is an extending arm 120 affixed at an end 120a to leg 41a. A trough 121 is provided proximate to end 120a of arm 120 which trough 121 is contiguous with the portion of leg 41 carrying bite block 90b. This arrangement provides a spring action to blocking surface 12a and further facilitates the ability of holder 10a to conform to different shapes of sensors.

Figure 9:
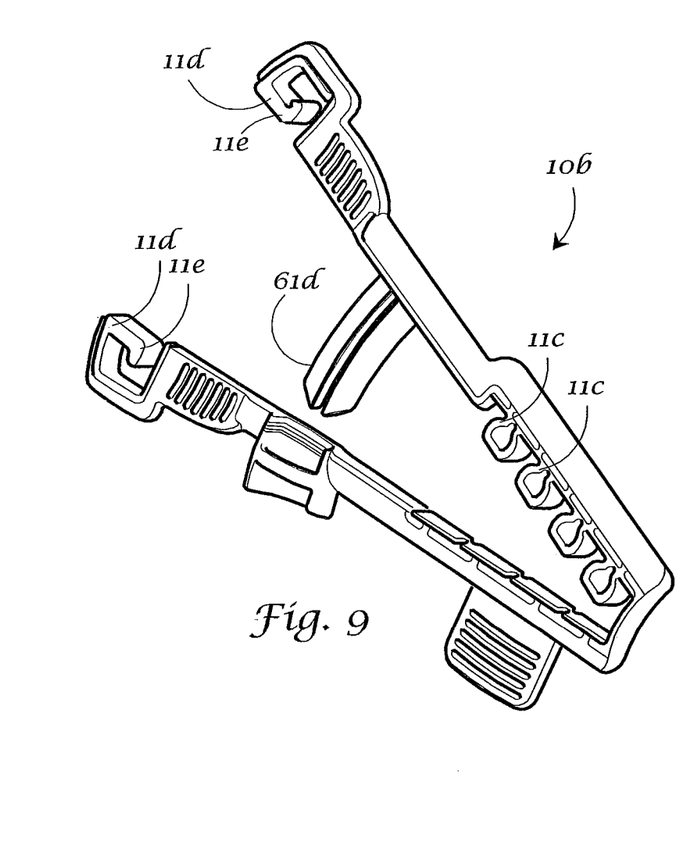
FIG. 9 is a perspective view of an alternative embodiment of a sensor holder according to the invention.

FIG. 9 shows another alternative embodiment of a sensor holder 10b according to the invention. In holder 10b, ratchet member 61d which has no detents as with ratchet members 61 and 61c, nor are there cooperating lugs carried by the other leg. Otherwise, ratchet member 61d operates in a manner similar to those other ratchet members discussed.

Holder 10b also shows a plurality of more irregularly shaped protrusions 11c and 11d. Protrusions 11d are more finger shaped having a lip 11e which serves to allow protrusions 11d to conform to a variety of sensor shapes and sizes. While protrusions 11, 11a, 11b, 11c and 11d have been depicted as being of generally uniform shape, a protrusion having a non-uniform, irregular shape is within the scope of the invention.

It should be apparent therefore that a holder for a dental x-ray sensor as depicted, described and otherwise exemplified herein is accomplished by the present invention. It will be understood that the present invention has been shown and described without attempting to disclose all embodiments and variations of the invention that are within the scope thereof.

What is claimed is:

1. A dental x-ray sensor holder comprising;
   (i) a bite block;
   (ii) at least two clamping faces wherein at least one of said faces comprises at least one resiliently deformable gripping protrusions, which is moveable towards a blocking surface on an opposing clamping face; said clamping faces are positioned in a moveable, spaced opposing relation, such that at least one of the faces is physically moved towards the other face to physically impinge the x-ray sensor therebetween;
   wherein a protrusion of the plurality of protrusions has a hollow interior portion that facilitates deformation; and
   wherein physical contact of the protrusion with the sensor causes the protrusion to at least partially deform.

2. A dental x-ray sensor holder as in claim 1, wherein each of said clamping faces includes said at least one gripping protrusion.

3. A dental x-ray sensor holder as in claim 1, wherein said at least one of said faces includes a plurality of said gripping protrusions.

4. A dental x-ray sensor holder as in claim 3, wherein said plurality of gripping protrusions are regularly or irregularly spaced in relation to each other.

5. A dental x-ray sensor holder as in claim 3, wherein at least one of said plurality of gripping protrusions is sized or shaped differently from at least one other of said plurality of gripping protrusions.

6. A dental x-ray sensor holder as in claim 1, wherein said at least one gripping protrusion is made of a material selected from the group consisting of rubber and plastic.

7. A dental x-ray sensor holder as in claim 1, wherein said at least one gripping protrusion has a shape selected from the group consisting of square, triangular, rectangular, cone-shaped, truncated cone shaped, spherical, box-like, round, ring or irregularly shaped.

8. A dental x-ray sensor holder as in claim 1, wherein said gripping protrusion is solid.

9. A dental x-ray sensor holder as in claim 1, wherein said gripping protrusion is hollow.

10. A dental x-ray sensor holder comprising a first leg hingedly connected to a second leg; each of said legs having a face positioned in a spaced, opposing relationship to the face of the other said leg, such that at least one of said faces of said legs is moved in relation to each other by the pivoting of at least one of said legs on said hinged connection therebetween; at least one of said faces comprising a plurality of ring-shaped hollow resiliently deformable gripping protrusions.

11. A dental x-ray sensor holder as in claim 10, further comprising means for locking said legs in a selected position relative to each other.

12. A dental x-ray sensor holder as in claim 11, wherein said means for locking includes a ratchet mechanism.

13. A dental x-ray sensor holder as in claim 11, wherein said hinge is a living hinge.

14. A dental x-ray sensor holder of the type to be used with a sensor having an attached cord, wherein the improvement comprises at least one clip attached to and positioned at a preselected position on the sensor holder; said clip being configured to secure said cord upon the sensor holder, wherein said sensor holder further includes a bite block and at least two clamping faces wherein at least one of said faces comprises a plurality of resiliently deformable hollow gripping protrusions, which is moveable towards a blocking surface on an opposing clamping face; said clamping faces are positioned in a moveable, spaced opposing relation, such that at least one of the faces is physically moved towards the other face to physically impinge the x-ray sensor therebetween.

15. A dental x-ray sensor holder as in claim 14, comprising a plurality of said clips such that said cord is secured in a plurality of selected positions upon the sensor holder.

16. A dental x-ray sensor holder as in claim 14, wherein at least one of said clips is removable and configured such that it is removed from a first selected position and reattached at another selected position upon the sensor holder.

* * * * *